US008688469B2

(12) United States Patent
Ziegler et al.

(10) Patent No.: US 8,688,469 B2
(45) Date of Patent: Apr. 1, 2014

(54) SYSTEM AND METHOD FOR IDENTIFYING A PROSPECTIVE CLINICAL THERAPY FOR A PROSPECTIVE PATIENT HAVING A MEDICAL DEVICE

(75) Inventors: Paul D. Ziegler, Minneapolis, MN (US); Shantanu Sarkar, Roseville, MN (US); Jodi L. Redemske, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 217 days.

(21) Appl. No.: 12/915,945

(22) Filed: Oct. 29, 2010

(65) Prior Publication Data

US 2012/0109675 A1    May 3, 2012

(51) Int. Cl.
*G06Q 10/00* (2012.01)
*G06Q 50/00* (2012.01)

(52) U.S. Cl.
USPC .................................................. 705/2; 705/3

(58) Field of Classification Search
USPC .......................................................... 705/2, 3
See application file for complete search history.

(56) References Cited

U.S. PATENT DOCUMENTS

2001/0053984 A1* 12/2001 Joyce et al. ........................ 705/2
2005/0192649 A1* 9/2005 Shehadeh et al. ............... 607/60
2005/0278001 A1* 12/2005 Qin et al. ........................ 607/48
2006/0026205 A1* 2/2006 Butterfield .................. 707/104.1
2008/0147440 A1* 6/2008 Kil ..................................... 705/2

OTHER PUBLICATIONS

Ziegler et al., Poster, "Prediction of Response to Ostial Pulmonary Vein Isolation by Analyzing Temporal Patterns of Atrial Tachyarrhythmia Burden".

* cited by examiner

*Primary Examiner* — Neha Patel
(74) *Attorney, Agent, or Firm* — Michael C. Soldner

(57) ABSTRACT

System and method for identifying a prospective clinical therapy for a prospective patient. The patient has a medical device, performed with a medical apparatus. The system has a historical database and an analyzer. The historical database incorporates information relating to a multiplicity of patients, each of the multiplicity of patients having a medical device and each of the multiplicity of patients having undergone a clinical therapy, the information including, for each of the multiplicity of patients, device characteristics of the medical device and an assessment of efficacy of clinical therapy. The analyzer correlates device characteristics of the prospective patient with the device characteristics and the assessment of efficacy of clinical therapy of the multiplicity of patients using the historical database to identify a prospective clinical therapy for the prospective patient associated with the device characteristics in the historical database having a relatively greater efficacy than the clinical therapy.

13 Claims, 9 Drawing Sheets

SYSTEM AND METHOD FOR IDENTIFYING A PROSPECTIVE CLINICAL THERAPY FOR A PROSPECTIVE PATIENT HAVING A MEDICAL DEVICE

FIELD

The present invention relates generally to systems and methods for identifying a prospective clinical therapy for a prospective patient and, in particular, to such systems and methods for identifying a prospective clinical therapy for a prospective patient having a medical device.

BACKGROUND

Medical devices for treating disease and symptoms of disease are well known in the art. Devices including, but not limited to, pacemakers, cardioverter/defibrillators, neurological stimulators, drug pumps, dialysis machines and ventilators may be associated with a patient suffering from an ailment and provide treatment for that ailment. Many such medical devices are actively controlled by electronics and are programmable, either to provide a constant treatment or to sense and adapt to patient conditions. These sorts of medical devices commonly, then, incorporate electronics to record patient data and diagnose patient conditions.

But the scope both of medical conditions and of available medical devices in the art is vast and may be very difficult for a medical professional to grasp in its entirety. The various specific ailments of each general category of medical condition may involve specific problems in each patient. Each type of medical device may include substantial numbers of variations to treat specific patient conditions. The myriad variations of each type of medical device may make the notionally straight-forward task of using a pacemaker to treat a patient suffering from bradycardia a vastly complicated task. Further, while some medical professionals receive years of training and experience to specialize in treating bradycardia, for instance, the same medical professional may not always be confronted with patient conditions solely within the medical professional's narrow expertise.

While health care systems have been developed to help consolidate the available treatment options with the known body of human ailments, such systems commonly involve either heavy reliance on general practitioners or teams of specialists analyzing individual patient conditions. While a general practitioner may have broad knowledge, and may be able to point treatment of a patient in the proper general direction, a general practitioner may not have the resources to provide a relatively highly effective medical device therapy to a patient suffering from a particular disease. Similarly, while teams of specialists may consider each patient, such teams involve substantial consumption of resources and are very expensive.

SUMMARY

Such methodologies of diagnosing patient conditions and arriving at appropriate treatment options do not typically utilize broadly available information and diagnostic techniques. By typically relying on the knowledge and experience of a few medical professionals, the scope of experience of a wider medical professional community with patients and potential patients across wide geographic and temporal frames may be minimal, generally limited to published writings. However, developments in medical device diagnostic and storage capabilities, combined with an ability to communicate over computer networks and the internet, have expanded the scope of how much medical information may be available for making and influencing treatment decisions.

A system for recommending potential clinical medical device therapies to a potential patient has been developed which utilizes diagnostic data obtained by medical devices and compiled in accessible databases. Throughout a system of disparate medical devices associated with various patients in various places at various times, patient conditions, applied treatments and efficacy of the treatments may be recorded by the medical devices. The medical devices may then transmit the recorded data to one or more accessible databases where the information may be made available to medical professionals for identifying potential therapies to apply to a patient who may be suffering from an ailment the same or similar to ailments suffered by other patients. Based on the effectivity of various applied therapies, decisions may be reached by the medical professional as to what therapies may effectively treat the medical professional's patient.

But the amount of data collected in the above described manner may be overwhelming if simply presented to a medical professional. Moreover, simply providing raw data does not provide a recommendation for how to treat a patient based on other patients who have been treated. A mere clearing-house of medical data does not ultimately resolve the problem of incomplete information, as thousands or more individual pieces of raw data are not commonly comprehendible by an individual trying to evaluate such information. Thus, the information in the database is correlated to diagnostic information from the prospective patient and an analyzer is configured to recommend a prospective therapy for treating the prospective patient based on the information in the database. As such, an automated system provides a medical professional not merely with information but rather with a recommended therapy to treat a prospective patient based on the treatments that have been applied to past patients and the success those therapies have had in treating those past patients. Such a system may provide a medical professional with time and money saving recommendations which the medical professional may not have had the expertise to develop on their own.

In an embodiment, a system for identifying a prospective clinical therapy for a prospective patient having a medical device, performed with a medical apparatus, has a historical database and an analyzer. The historical database incorporates information relating to a multiplicity of patients, each of the multiplicity of patients having a medical device and each of the multiplicity of patients having undergone a clinical therapy, the information comprising, for each of the multiplicity of patients, device characteristics of the medical device and an assessment of efficacy of clinical therapy. The analyzer correlates device characteristics of the prospective patient with the device characteristics and the assessment of efficacy of clinical therapy of the multiplicity of patients using the historical database to identify a prospective clinical therapy for the prospective patient associated with the device characteristics in the historical database having a relatively greater efficacy than the clinical therapy.

In an embodiment, the historical database incorporates information relating to patient characteristics of each of the multiplicity of patients. The analyzer correlates device characteristics of the prospective patient with the device characteristics, the patient characteristics and the assessment of efficacy of clinical therapy of the multiplicity of patients and identifies, using the historical database, a prospective clinical therapy for the prospective patient associated with the device characteristics in the historical database having a relatively greater efficacy.

In an embodiment, each of the multiplicity of patients have undergone at least one of a plurality of clinical therapies, wherein the analyzer identifies a prospective clinical therapy for the prospective patient associated with the device characteristics and the patient characteristics having a relatively greater efficacy than at least one of the plurality of clinical therapies.

In an embodiment, the system further has an output configured to provide the prospective clinical therapy to a user.

In an embodiment, the device characteristics are at least one of atrial tachycardia burden, atrial fibrillation burden, atrial tachycardia episode duration, atrial fibrillation episode duration, ventricular rate during at least one of atrial tachycardia and atrial arrhythmia, patient activity, heart rate, heart rate variability, defibrillation shocks, ventricular tachycardia, ventricular fibrillation, attempts at ventricular antitachycardia pacing, success at ventricular antitachycardia pacing, attempts at atrial antitachycardia pacing, success at atrial antitachycardia pacing, thoracic impedance, respiration, pressure, heart sounds, electrocardiogram timing, electrocardiogram morphology, proportion of atrial pacing, proportion of ventricular pacing, bradycardia episodes, asystole episodes, premature atrial contractions, premature ventricular contractions, patient inputs indicative of symptomatic episodes and patient-initiated shocks.

In an embodiment, the patient characteristics are at least one of age, gender, body mass index, weight, blood pressure, prior hospitalizations, family history of disease, symptom status, New York Heart Association classification, medications being taken, prior cardiovascular surgeries/procedures, left ventricular ejection fraction, left atrial diameter, cardiac output, left ventricular chamber dimensions, values indicative of quality of life, functional capacity measure, CHADS2 score, congestive heart failure, diabetes, hypertension, prior stroke or transient ischemic attack, coronary artery disease, atrial tachyarrhythmia, ventricular tachyarrhythmia, bradycardia, valvular disease and myocardial infarction.

In an embodiment, the correlating step is accomplished utilizing statistical analysis.

In an embodiment, the statistical analysis comprises Bayesian methods.

In an embodiment, the statistical analysis comprises self-organizing maps.

In an embodiment, a method identifies a prospective clinical therapy for a prospective patient having a medical device, performed with a medical apparatus. Device characteristics from the medical device of the prospective patient are obtained with the medical apparatus. A historical database incorporating information relating to a multiplicity of patients is accessed with the apparatus, each of the multiplicity of patients having received a medical device and each of the multiplicity of patients having undergone a clinical therapy, the information comprising, for each of the multiplicity of patients, device characteristics of the medical device and an assessment of an efficacy of the clinical therapy. The device characteristics of the prospective patient are correlated by the medical apparatus with the device characteristics and the assessment of efficacy of clinical therapy of the multiplicity of patients. A prospective clinical therapy for the prospective patient is identified using the historical database and being associated with the device characteristics in the historical database based, at least in part, on the correlation, of the prospective clinical therapy having a relatively greater efficacy than the clinical therapy.

In an embodiment, the method has the additional step of obtaining, with the medical apparatus, patient characteristics from the prospective patient. The correlating step further also correlates the patient characteristics of the prospective patient with the device characteristics, the patient characteristics and the assessment of efficacy of clinical therapy of the multiplicity of patients. The identifying step further identifies, using the historical database, the prospective clinical therapy for the prospective patient associated with the device characteristics and the patient characteristics in the historical database based, at least in part, on the correlation, of the prospective clinical therapy having a relatively greater efficacy than the clinical therapy.

In an embodiment, each of the multiplicity of patients have undergone at least one of a plurality of clinical therapies, the correlating step comprises correlating the patient characteristics of the prospective patient with the device characteristics, the patient characteristics and the assessment of efficacy of at least one of the plurality of clinical therapies of the multiplicity of patients, and the identifying step comprises identifying, using the historical database, the prospective clinical therapy for the prospective patient associated with the device characteristics and the patient characteristics in the historical database based, at least in part, on the correlation, of the prospective clinical therapy having a relatively greater efficacy than at least one of the plurality of clinical therapies.

In an embodiment, the method has the further step of creating the historical database incorporating information relating to a multiplicity of patients, each of the multiplicity of patients having received a medical device and each of the multiplicity of patients having undergone at least one of a plurality of clinical therapies, the information comprising, for each of the multiplicity of patients, device characteristics of the medical device, patient characteristics and an assessment of an efficacy of at least one of the plurality of clinical therapies.

In an embodiment, the method has the further step of recommending, with the medical apparatus, to a physician the prospective clinical therapy.

FIGURES

DESCRIPTION

Figure 1:
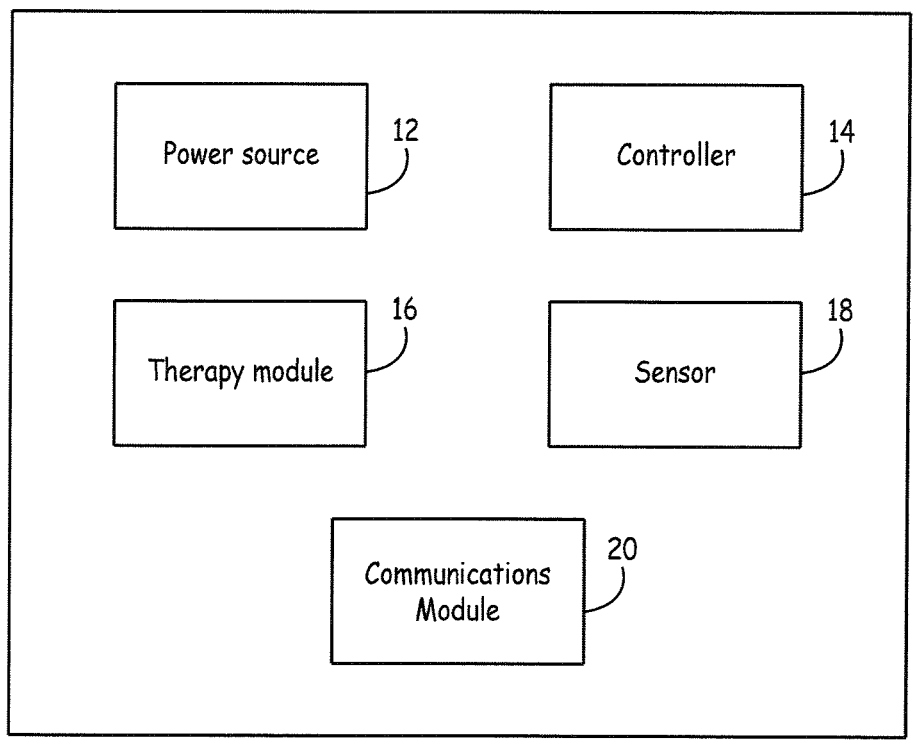
FIG. 1 is a block diagram of a generic medical device.

FIG. 1 is a block diagram of generic active medical device 10. Medical device 10 may be any of myriad active medical devices well known in the art, including, but not limited to, pacemakers, cardioverter/defibrillators, neurological stimulators, drug pumps, dialysis machines and ventilators. Such medical devices commonly include componentry such as power source 12, controller 14, therapy module 16, sensor 18 and communication module 20. Various specific embodiments of medical device 10, including specific embodiments of the types of medical device 10 listed above, may include more or fewer componentry as appropriate. For instance, various pacemakers and cardioverter/defibrillators incorporate a memory module for storage of sensor data. Alternatively, certain medical devices 10 may be sensors configured to diagnose but not to treat a patient and configured with sensor 18 but not therapy module 16. Components of medical device 10 may be selected and configured in accordance with technology well known in the art. Additional components may also be utilized for medical device 10 or components illustrated may be omitted, again in accordance with well known technology or technology developed in the future.

As well known in the art, power source 12 may provide power to allow the operation of medical device 10 and may be a self-contained power source such as a battery or may derive power from an external source, such as commonly available line or another external power source, such as by inductive coupling. Self-contained power sources are common among implantable medical devices while external power sources are common among external medical devices. Controller 14 may incorporate various electronics useful for controlling the performance of medical device 10, including, but not limited to, processors, microcontrollers, digital memory and system clocks. Controller 14 may be directly responsible for the high-level functionality of medical device 10.

Therapy module 16 may be based on the type of medical device 10 in which therapy module 16 is incorporated. In pacemakers and cardioverter/defibrillators, therapy module 16 may be configured to deliver varying levels and types of electrical stimulation to a patient beyond conventional pacing, for instance ventricular antitachycardia pacing and atrial antitachycardia pacing. In drug pumps, therapy module 16 may be configured to store and regulate the delivery of therapeutic substances to the patient. In a ventilator, therapy module 16 may merely pump air or other appropriate gasses in a regulated way. In addition, therapy module 16 may provide multiple different types of therapy. As known in the art, cardioverter/defibrillators may deliver high voltage electrical shocks as well as low voltage pacing therapy, each of which may involve separate therapy delivery circuitry. In addition, medical device 10 may incorporate therapy modules 16 with multiple different types of therapy delivery, for instance a combination of drug delivery and electrical stimulation. Other types of therapy modules 16, in existence or to be developed, may also be utilized.

As with therapy module 16, sensor 18 may be any of various sensors well known in the art, including sensors to detect electrical signals generated by a patient's heart, blood pressure sensors, respiration sensors, insulin levels and so forth. Sensor 18 may incorporate multiple such sensors. In various embodiments, sensor 18 is sensitive to physiologic parameters such as atrial tachycardia and atrial fibrillation burden or episode duration, ventricular rate during atrial tachycardia and atrial fibrillation, patient activity, heart rate during both day and night, heart rate variability, ventricular tachycardia and ventricular fibrillation episodes, thoracic impedance, respiration, pressure, heart sounds, electrogram timing and morphology, bradycardia episodes, asystole episodes, premature atrial contractions and premature ventricular contractions. Such information may be included in device characteristics identifiable by medical device 10. In various embodiments of medical device 10, controller 14 may initiate therapy delivery to the patient on the basis of output from sensor 18. Alternatively, in embodiments of medical device 10 in which sensor 18 is not present, controller 14 may deliver therapy automatically and without regard to patient condition. Other types of sensor modules 16, in existence or to be developed, may also be utilized.

Medical device 10 may further incorporate communication module 20. In various embodiments, communication module 20 may provide for direct user input to program medical device 10 to deliver particular therapy or to obtain sensor information. Such communication module 20 may incorporate a display screen and a keyboard, touchscreen or other device by which information may be input to or obtained from medical device 10. In addition, communication module 20 may incorporate telemetry communications or other modes of electronic data transmission well known in the art. Such communications may be wireless or over wires and may be local or over a network. In various embodiments, communication module 20 incorporates an ability to transmit patient data over the interne, either directly or by way of a relay station which receives the information from medical device 10 and retransmits the information over the interne to a distant location. Other types of communication modules 20, in existence or to be developed, may also be utilized.

Figure 2:
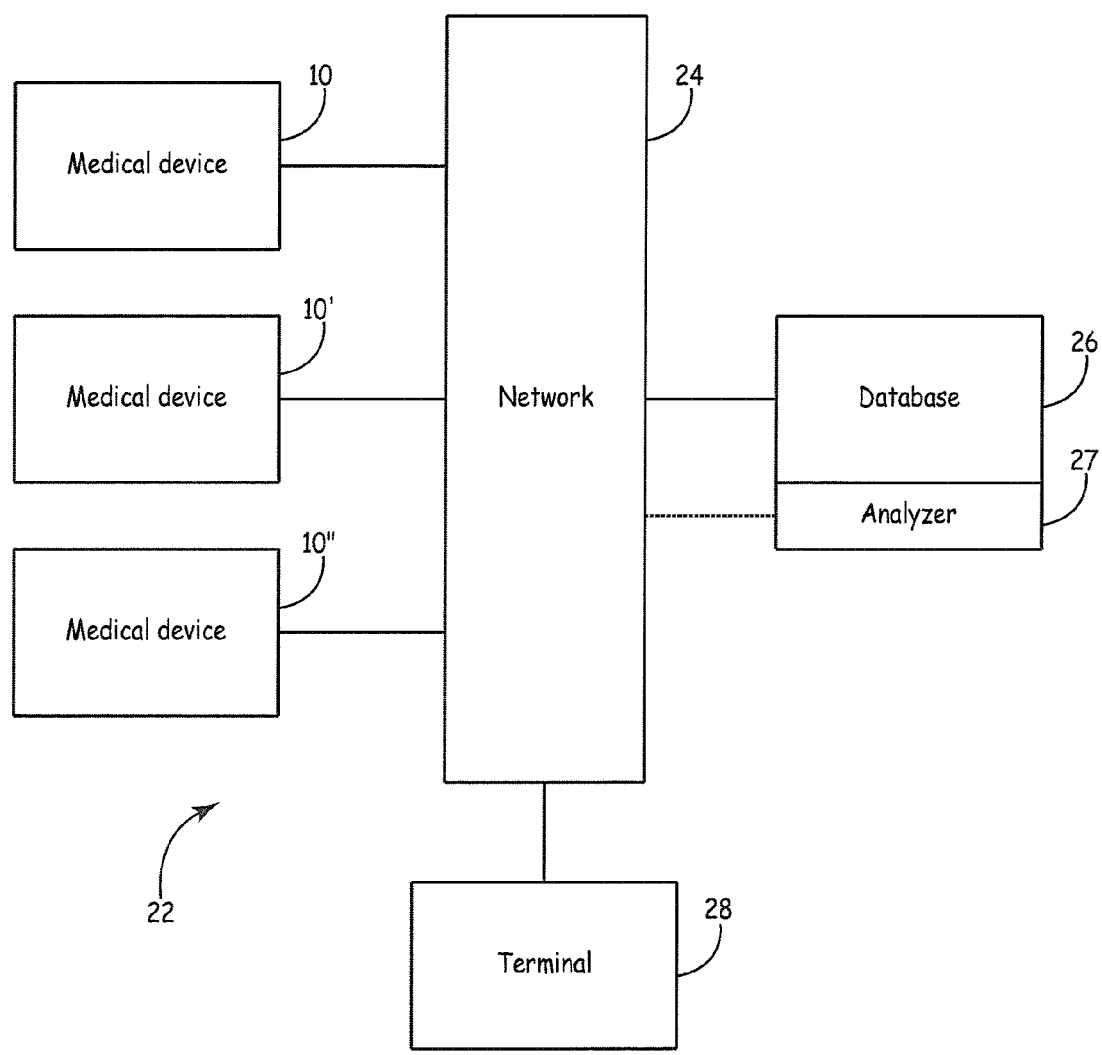
FIG. 2 is a block diagram of a system for identifying a prospective clinical therapy for a prospective patient.

FIG. 2 is a diagram of medical apparatus system 22 which incorporates multiple medical devices 10, 10', 10", etc., configured to communicate over network 24 to historical database 26. System 22 further may incorporate terminal 28 likewise coupled to network 24. Medical devices 10, 10', 10" may be medical devices known in the art and may conform with, though not necessarily be limited by the various embodiments of medical device 10 described above. Medical devices 10, 10', 10" may be coupled to network 24 according to various methods known in the art, including those described with respect to communication module 20 above.

Network 24 is selected among various networks known in the art and may incorporate multiple networks operating in series, parallel or both. Medical devices 10, 10', 10" and network 24 incorporate variably proprietary and commercial standard hardware to facilitate network communications. Included in network 24 may be the interne and local networks. In various embodiments, a medical device 10 may be coupled directly to the internet which may be coupled directly to database 26. Alternatively, medical device 10 may be coupled to a local network which may be coupled to the internet, while database 26 is similarly coupled to a local network which is coupled to the internet. In various embodiments, some of medical devices 10, 10', 10" are coupled directly to the interne while others of medical devices 10, 10', 10" are coupled to a local network which is coupled to the internet. In alternative embodiments, network 24 is purely one or more local networks which operate without respect to the internet.

Historical database 26 incorporates information detailed below. Database 26 exists on electronically accessible equipment as known in the art. Such electronically accessible equipment may include conventional computer hardware, network servers and data storage devices. Database 26 may exist on one electronically accessible device or may be divided or may be redundantly stored on multiple such devices. While database 26 may exist on equipment which has little or no processing capabilities, database 26 may advantageously exist on equipment which either has or is closely coupled to electronic equipment which has analyzer 27 sufficient to manipulate and analyze the information in database 26 as described below.

Terminal 28 may be coupled to database 26 by way of network 24. In various embodiments, terminal 28 is a conventional, commercially available computer well known in the art. In alternative embodiments, terminal 28 is a commercially available or proprietary device which lacks many of the conventionally available components of a computer, though may still incorporate a user input/output to display data to a user and accept user instructions. In embodiments in which terminal 28 incorporates an analyzer, terminal 28 may process data from database 26. In embodiments in which terminal 28 incorporates electronic storage, terminal 28 may store all or part of database 26.

Figure 3:
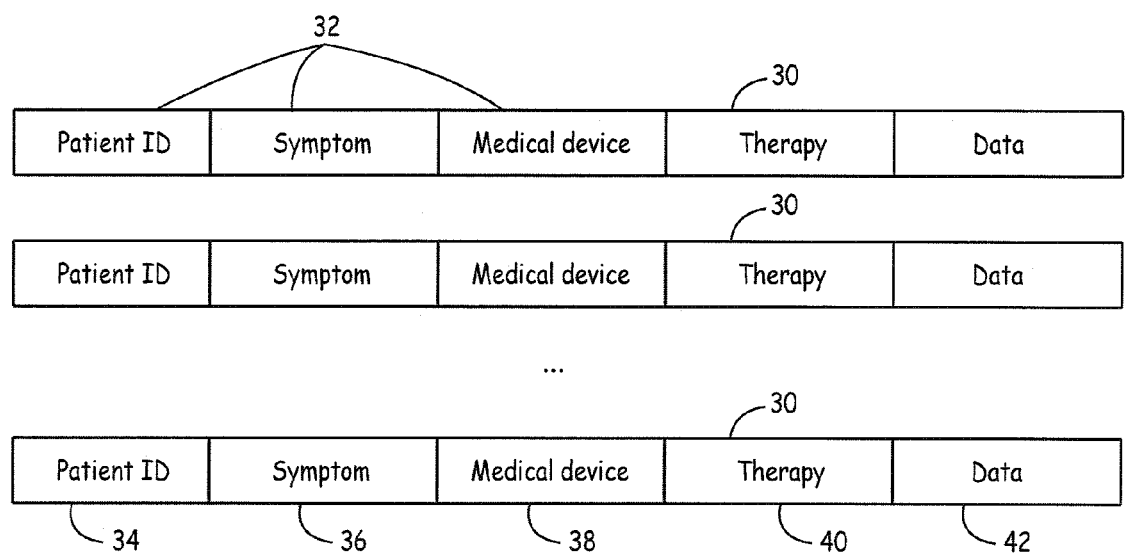
FIG. 3 is a block diagram of fields for a database from the system of FIG. 2.

FIG. 3 is a simplified, block-level illustration of entries 30 in database 26. Each entry 30 incorporates multiple fields 32 which may be individually configurable to store particular types of data from medical devices 10, 10', 10" and in various embodiments, other sources. In the illustrated, simplified embodiment, each entry 30 incorporates patient identification field 34, symptom field 36, medical device field 38, delivered therapy field 40 and data field 42.

Patient identification field 34 may incorporate a unique identifier for the patient in question. Patient identification field 34 may further incorporate patient characteristics such as, but not limited to, demographic information including age, gender, body mass index, weight, blood pressure, prior hospitalizations, family history of disease, symptom status, medications being taken and prior cardiovascular surgeries or procedures.

In various embodiments, additional fields 32 may be incorporated, including, though not necessarily limited to, date fields, a unique identifier field, and multiple additional, unique fields for symptoms 36, medical device identification 38, delivered clinical therapy field 40 and data field 42 pertaining in particular to an assessment of an efficacy of the delivered clinical therapy. In particular, patients who suffer multiple symptoms, have multiple devices 10, 10', 10" or, in particular, who have multiple delivered therapies with resultant data, may have multiple fields assigned for each medical device and/or each delivered therapy or therapeutic result.

In addition, additional fields may be incorporated which provide patient characteristics which do not come from medical devices 10, 10', 10" but which may be relevant to diagnosing the patient. Such patient characteristics may include the patient's New York Heart Association (NYHA) classification, left ventricular ejection fraction, left atrial diameter, cardiac output, left ventricular chamber dimensions, quality of life scores, a functional capacity measure such as a six (6) minute hall-walk and $CHADS_2$ score. Additional, comorbid patient conditions which may be stored include congestive heart failure, diabetes, hypertension, prior stroke or transient ischemic attack, coronary artery disease, atrial tachyarrhythmias, ventricular tachyarrhythmias, bradycardia, valvular disease, myocardial infarction.

As will be readily understood, database 26 is scalable to very large data sizes. Database 26 may be populated by way of system 22, with information from medical devices 10, 10', 10" being used to populate database 26. In various embodiments, medical devices 10, 10', 10" advantageously automatically transmit data to database 26 via network 24 or are prompted to transmit data to database 26. Alternatively, information may be manually input into database 26, for instance at terminal 28 or directly at database 26. Such information may include device characteristics pertaining to the use of medical devices 10, 10', 10" by the patient, such as symptomatic episodes or patient-initiated shocks. In such an embodiment, terminal 28 may be a patient controlled device.

In various embodiments, at least some of medical devices 10, 10', 10" are configured to transmit data to database 26 at regular intervals. In various embodiments, at least some of medical devices 10, 10', 10" are configured to transmit data to database 26 based on the occurrence of trigger conditions. In various embodiments, at least some of medical devices 10, 10', 10" are configured to transmit data to database 26 based on a user prompt. In various embodiments, some or all of these conditions are utilized to cause data to be transmitted to database 26, while additional conditions for transmission of data to database 26 are contemplated.

To illustrate the transmission of data to database 26, ultimately, the use of database 26 to obtain a recommended therapy for a prospective patient, an exemplary embodiment involving medical device 10' being an implantable pacemaker is provided. Implantable pacemaker 10' incorporates pacing therapy module configured to treat atrial fibrillation 16, electrogram sensor 18 and a communications module 20 comprising an internal wireless telemetry module and an external communicator configured to transmit information to network 24. It is emphasized that the following is illustrative only and it will be readily appreciated by one of ordinary skill in the art that database 26 and system 22 generally are readily configurable for various types of medical devices 10, 10', 10" known in the art. In particular, in the exemplary embodiment, data in database 26 will be illustrated that relates to the effectivity of ablation in treating atrial fibrillation.

Collection of data in database 26 for the exemplary embodiment described above is illustrated in the flowchart of FIG. 4. In an embodiment, a patient is implanted (400) with implantable pacemaker 10' which transmits (402) data to database 26. In the exemplary embodiment, the data corresponds to entry 30 including a unique patient identifier 30, that the patient is suffering from atrial fibrillation for symptom field 36, an identification of implantable pacemaker 10' by model number and, in an embodiment, a unique identifier for that particular implantable pacemaker 10' and the therapy settings to which implantable pacemaker 10' has been set for therapy delivered field 40. In various embodiments, database 26 formats (404) the data received from implantable pacemaker 10' into entry 30 and stores (406) entry in database 26. Optionally, formatting step (404) either does not occur or does not occur in database 26.

In the exemplary embodiment, the heart of the patient is then ablated (408) with ablation device 10". In the exemplary embodiment, the ablation procedure is a pulmonary vein isolation procedure well known in the art. In an embodiment, ablation device 10" transmits (410) data to database 26. Alternatively, a medical professional enters the data manually using terminal 27. In such embodiments, the data corresponds to entry 30 including the unique patient identifier, that the patient is suffering from atrial fibrillation for symptom field 36, an identification of ablation device 10" by model number and, in an embodiment, a unique identifier for that particular ablation device 10" and the therapy which was applied to the patient for the therapy delivered field 40. As with implantable pacemaker 10', database 26 formats (412) the data received from implantable pacemaker 10' into entry 30 and stores (414) entry in database 26. Optionally, formatting step (412) either does not occur or does not occur in database 26.

In certain variations of the exemplary embodiment, the ablation (408), transmission (410), formatting (412) and storage (414) steps may be performed before the steps pertaining to implantable pacemaker 10'. In addition, particularly with respect to ablation device 10", which may, in certain embodiments, not have communication module 20 which incorporates a capacity to transmit data directly to network 24, a medical professional may input the relevant data pertaining to the ablation procedure using terminal 28.

Figure 5:
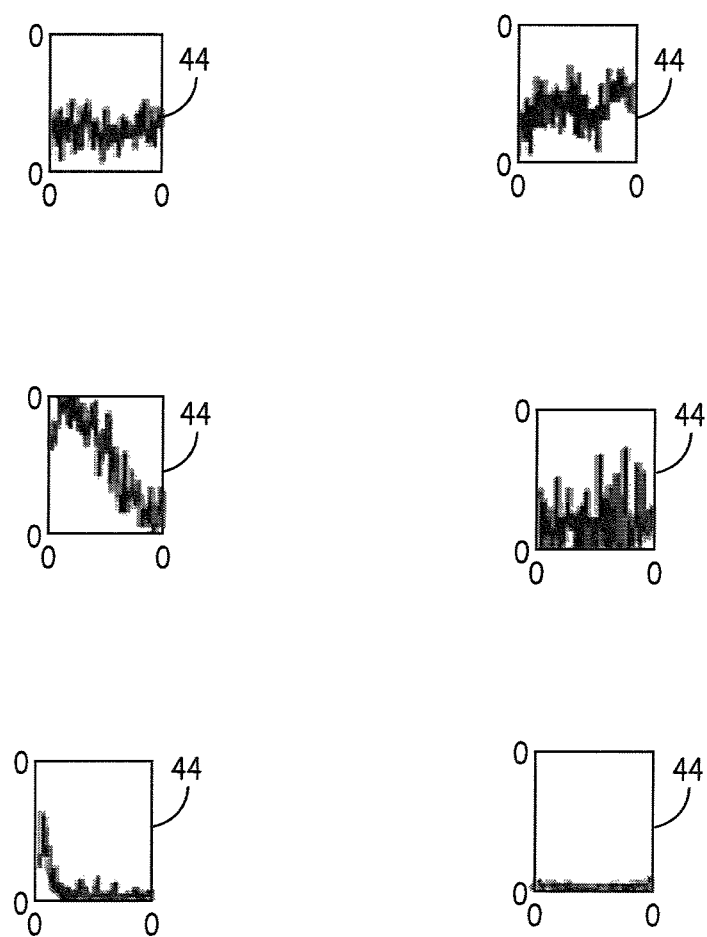
FIG. 5 is an illustration of an arrhythmia burden.

In the exemplary embodiment, implantable pacemaker 10' may make further data transmissions (416) as described above, both before the conduction of ablation procedure (408) and after. Otherwise, storing of data for a particular patient may end (418). In the exemplary embodiment, additional transmissions are provided with a unique entry 30 in database 26. In such instances, data field 42 may be stored with data pertaining to the occurrence of atrial fibrillation in the patient, in particular data pertaining to an amount of time per day the patient has been in atrial fibrillation, known in the art as an arrhythmia burden, and/or a graphical representation of the arrhythmia burden of the patient, known in the art as an arrhythmia burden pattern and illustrated as exemplary burden patterns 44 in FIG. 5.

As discussed above, database 26 is configured to store data from multiple patients having various medical conditions, various medical devices, various therapeutic treatments and various results. Repeating the processes outlined in FIG. 4 across multiple patients may result in database 26 being adequately populated to allow some or all of the information in database 26 to be subjected to a statistical analysis using, in an embodiment, analyzer 27.

In various embodiments, analyzer 27 is configured to apply various statistical analysis techniques known in the art. In an embodiment, analyzer 27 applies a self-organizing map technique known in the art. In an alternative embodiment, analyzer 27 applies a Bayesian statistical method, such as a Bayesian belief network, known in the art. In various alternative embodiments, analyzer 27 applies various alternative statistical analysis techniques known in the art.

Briefly, a Bayesian belief network combines multiple sources of information to be able to create a discriminator for diagnostic purposes. Utilizing database 26, a Bayesian belief network may combine various information stored in database 26, detailed above, and then create a discriminator that can provide a recommendation for different therapies based of our knowledge for different responders. According to the Bayesian belief network methodology know in the art, based on information from database 26, a probability$_{evidence|therapy\ response}$ and a probability$_{therapy\ response}$ are available and are used to determine probability$_{therapy\ response|evidence}$. The evidence is derived from device characteristics and patient characteristics detailed above. The one output of the Bayesian belief network with the largest probability for a given set of evidence may be recommended, as detailed below with respect to the self-organizing map embodiment.

For the purposes of illustration, the above-detailed exemplary embodiment involving the treatment of atrial fibrillation will be shown being subjected to a self-organizing map technique. It is emphasized that this exemplary embodiment is not limiting, and a person of ordinary skill in the art will readily understand how the particular embodiment illustrated here may be applied to symptoms, therapies and data analysis techniques known in the art. Such therapies include, but are not limited to, pulmonary vein isolation, pulmonary vein isolation with additional linear lesions, antiarrhythmic drug therapy, rate control drug therapy, AV nodal ablation, diuretic drugs, hypertension medication, anticoagulation therapy, left atrial appendage occlusion devices, coronary stents, continuous positive airway pressure devices, bradycardia pacing, cardiac resynchronization therapy and implantable cardioverter defibrillators.

Figure 6A:
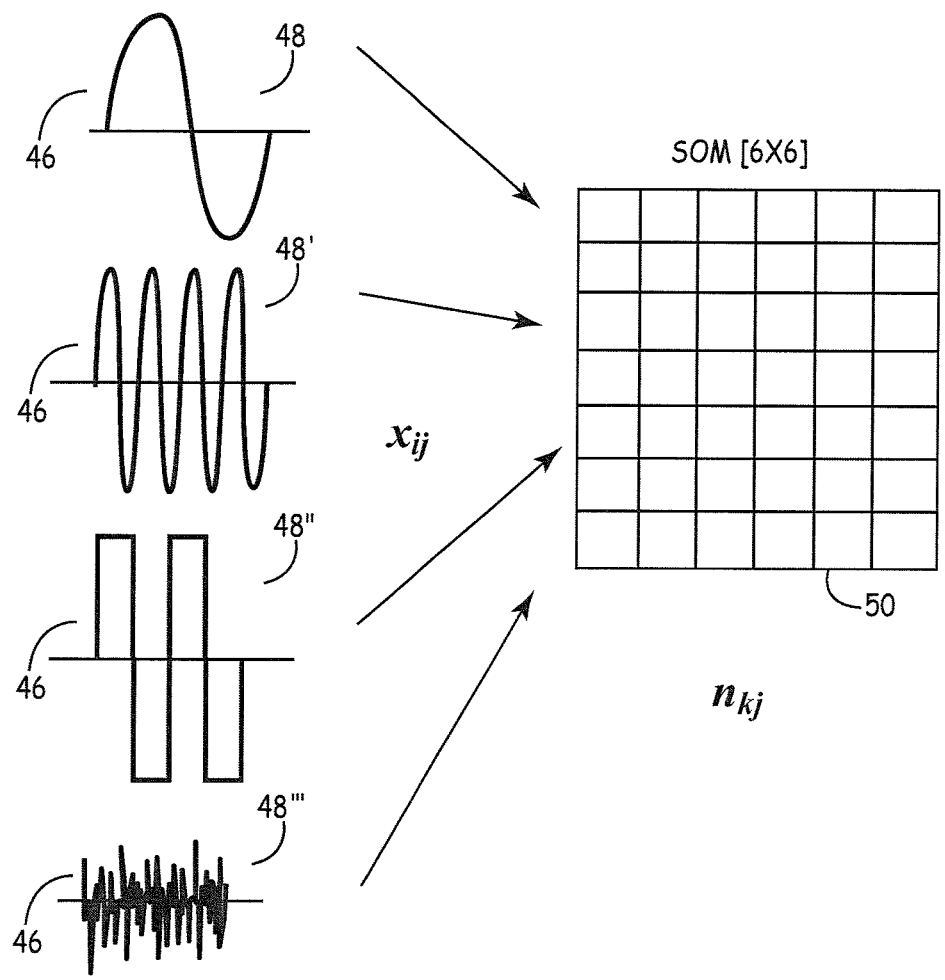
FIGS. 6a, 6b and 6c are graphical depictions of performing a self-organizing map procedure.
Figure 6B:
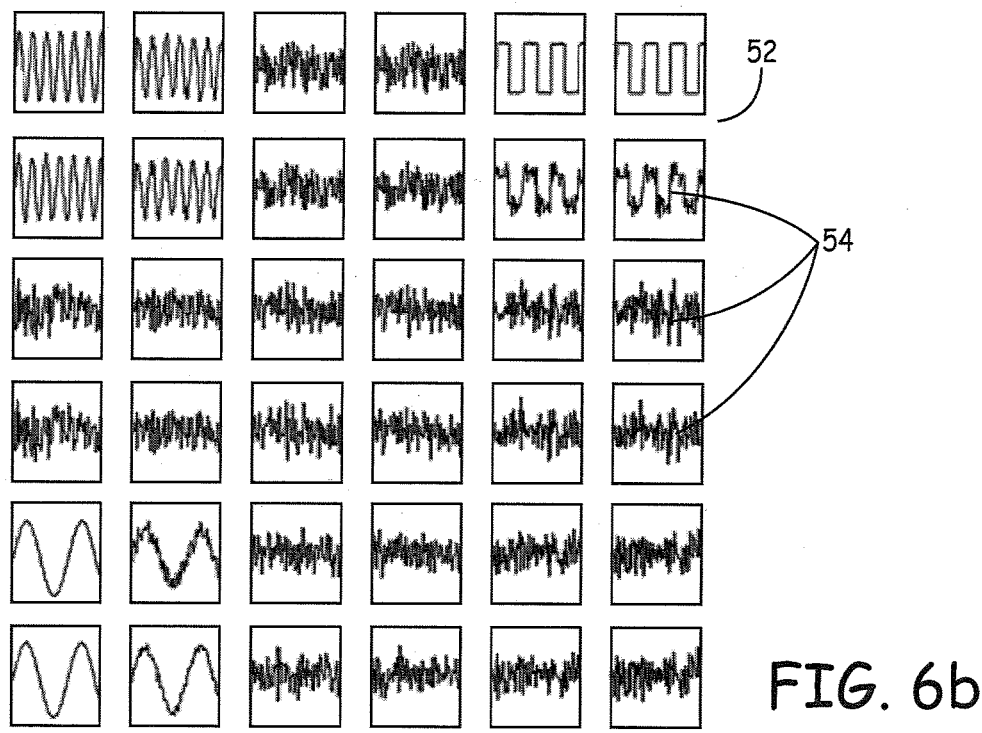
Figure 6C:
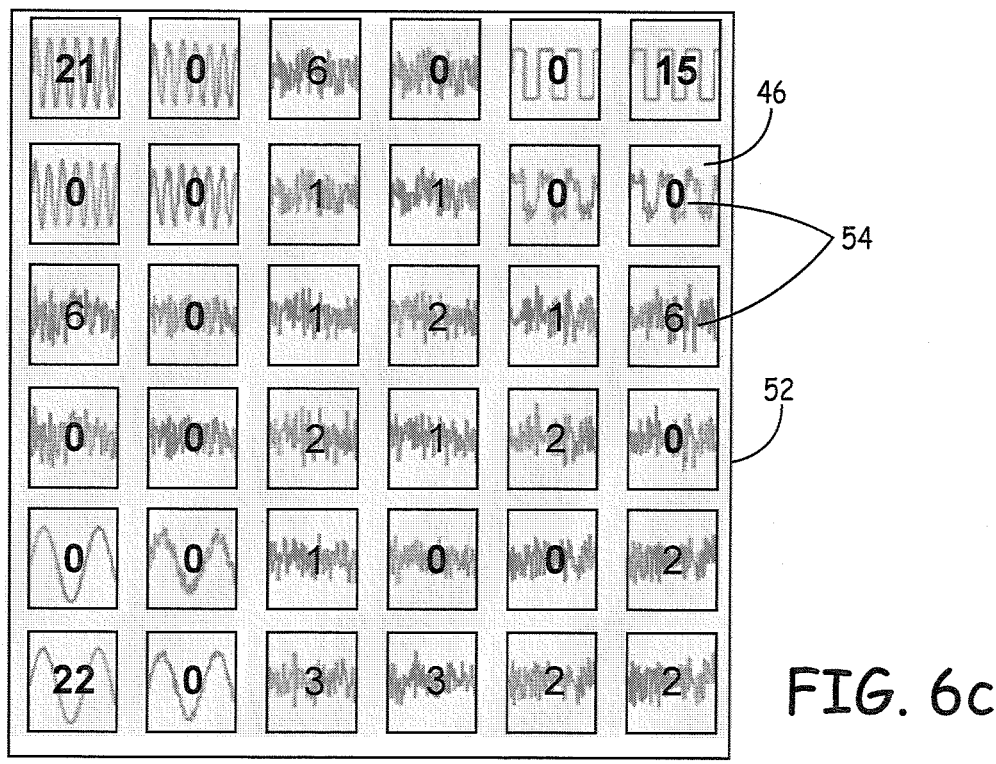

FIGS. 6a, 6b and 6c provide a generic demonstration of a self-organizing map. Various input signals 46 are organized into classes 48, 48', 48", 48'. In the illustrated embodiment, signals 46 are then organized onto a six-by-six map 50 according to methodologies known in the art. First, map 50 is initialized by spreading signals 46 throughout map 50 randomly. Second, a minimum distance between signals 46 on map are computed according to the equation:

$$d_{ik} = \sqrt{\sum_j (x_{ij} - n_{kj})^2}$$

Third, the map 50 is updated by rearranging signals 46 on map 50 according to the equations:

$$n_{kj} = n_{kj} + h(t)(x_{ij} - n_{kj})$$

$$h(t) = \left(1 + \frac{t-1}{N}\right)^{-1}$$

Applying the above described, non-parametric recursive regression to signal classes 48, 48', 48", 48'" produces arranged map 52 organized generally in FIG. 6b and detailed according to a number of signals 46 in each node 54 of arranged map 52 in FIG. 6c and forms a self-similarity graph. Each node 54 represents a data model to which each signal 46 may correspond. Thus, the self-organizing map converges to arranged map 52 with each signal 46 associated with one node 54 in arranged map 52 with similar signals 46 being associated with the same or neighboring node 54.

Figure 7A:
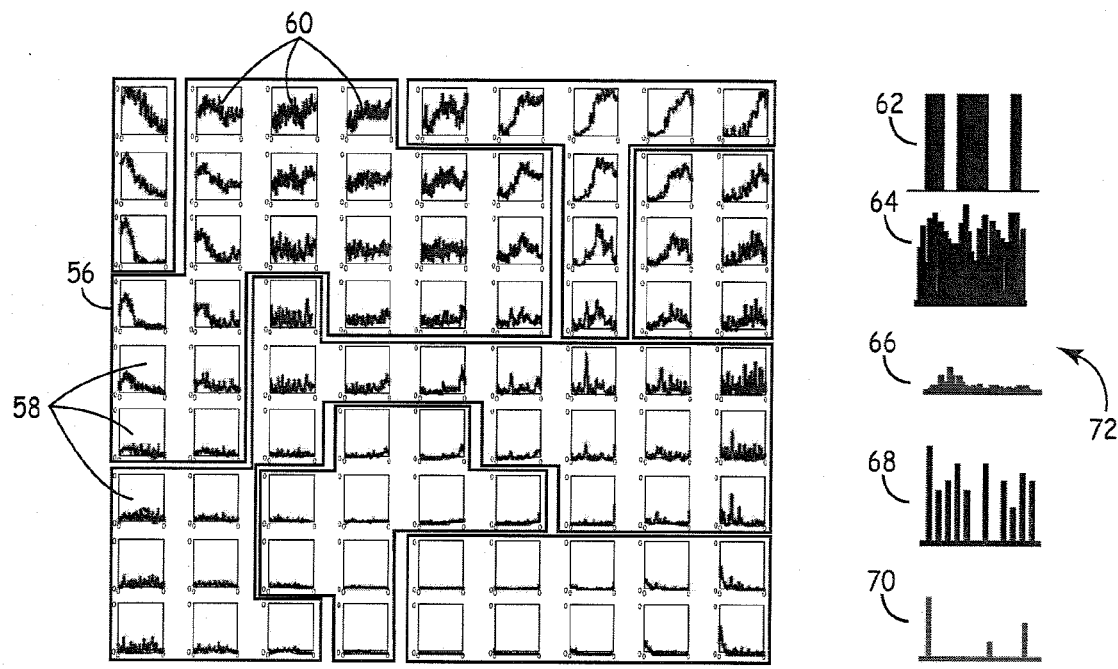
FIGS. 7a and 7b illustrate utilizing the self-organizing map procedure of FIGS. 6a, 6b and 6c to analyze arrhythmia burden.
Figure 7B:
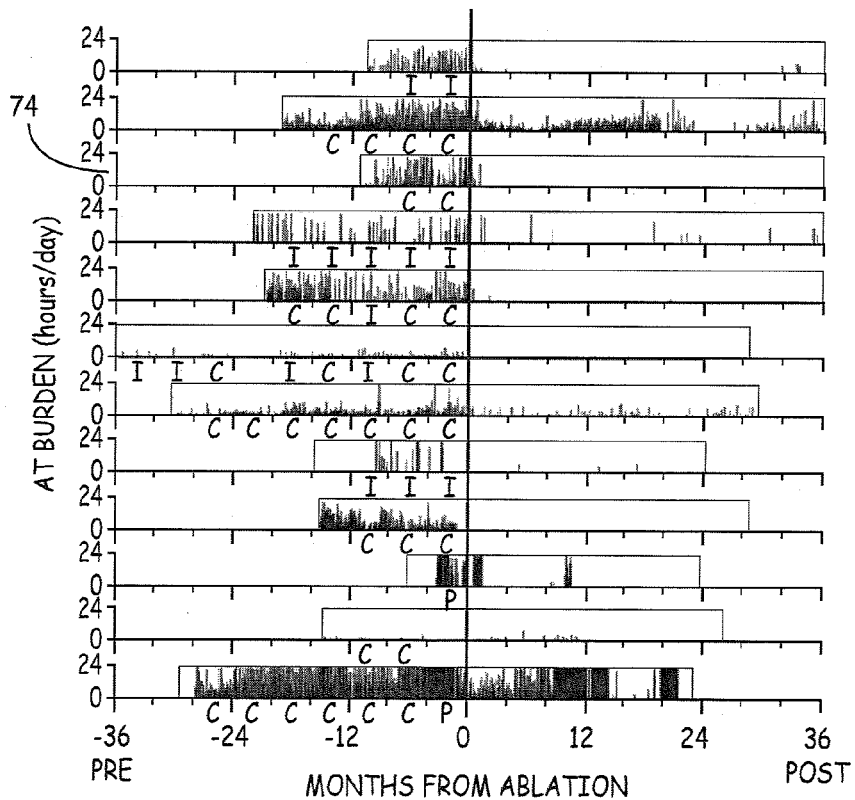

In the exemplary embodiment pertaining to atrial fibrillation, FIGS. 7a and 7b illustrate an arranged, nine-by-nine map 56 of atrial fibrillation arrhythmia burden samples 58 from twelve patients. According to the process illustrated in FIGS. 6a, 6b and 6c, arrhythmia burden samples 58 are arranged on map 56. Each burden sample 58 is regressed against each data model 60 of map 56 iteratively. Dominant patterns are determined based on the number of arrhythmia burden samples 58 corresponding to each data model 60, as illustrated in FIG. 6c. On the basis of the number of hits, patterns 62, 64, 66, 68, 70 of neighboring models 60, corresponding to legend 72, are identified according to the self-organizing map technique and other techniques known in the art. In various embodiments, identification techniques include k-means clustering and visual inspection by a medical professional.

Each of the various patterns are evaluated on the basis of the frequency of arrhythmia burden. As illustrated, persistent arrhythmia burden P corresponding to pattern 62, contiguous arrhythmia burden C corresponding to patterns 64, 66 and intermittent arrhythmia burden I corresponding to patterns 68, 70. On the basis of the arranged and categorized arrhythmia burden samples 58, the categorized burden samples 58 are arranged, for the purposes of illustration in this exemplary embodiment, in chart 74 by order in time and patient number according to FIG. 7b. It is noted that arranging arrhythmia burden samples 58 into chart 74 may not be necessary for analyzer 27 to conduct its analysis, and may, in fact, not be performed at all in most embodiments.

Figure 4:
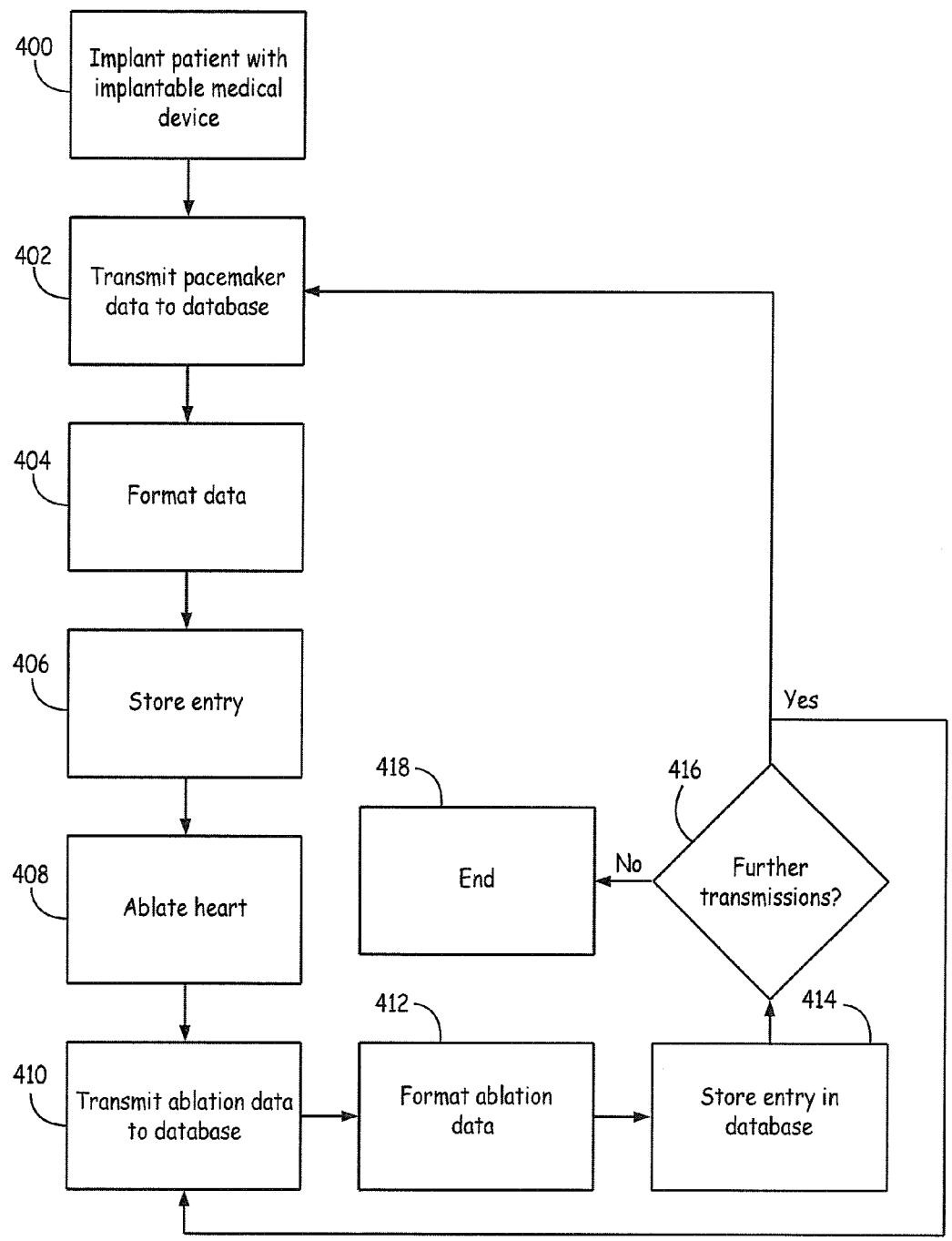
FIG. 4 is a flowchart detailing populating the database illustrated in FIG. 3.

As illustrated according to chart 74, each patient has arrhythmia burden samples 58 which are indicative of either a persistent, contiguous or intermittent arrhythmia both before and after the conduction of an ablation procedure (408)(FIG. 4). By comparing a difference in arrhythmias before and after the ablation procedure, a binary effectivity 76 of the ablation procedure is obtained for each patient.

Figure 8:
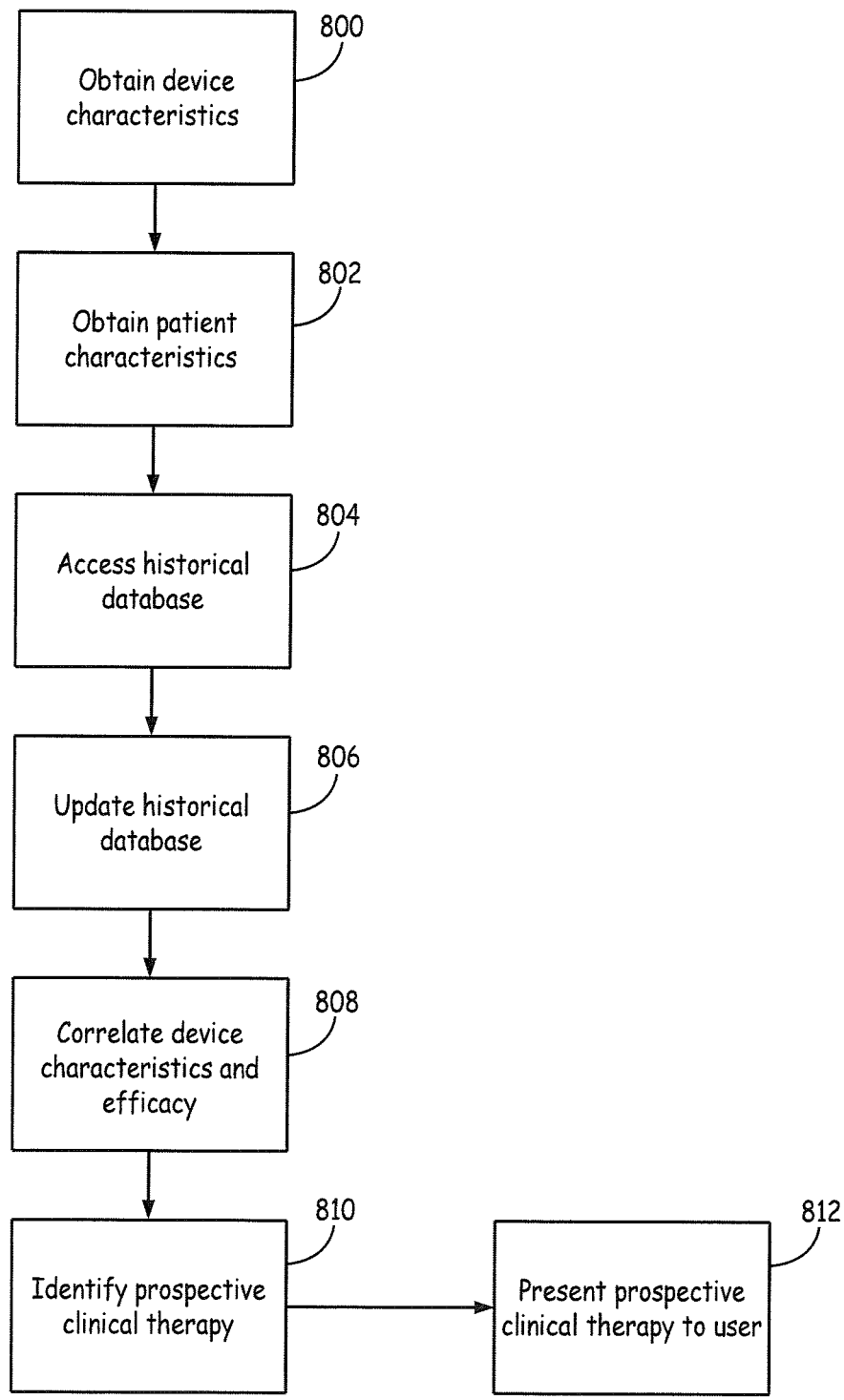
FIG. 8 is a flowchart for recommending a clinical therapy to a prospective patient.

FIG. 8 provides a method for utilizing database 26 and analyzer 27 to determine whether a particular prospective patient for a particular clinical therapy should receive the clinical therapy. The exemplary embodiment pertaining to treating atrial arrhythmia will be maintained for illustrative purposes, but it is again emphasized that a person of ordinary skill in the art would be able to apply the following methodology to patient conditions and clinical therapies known in the art.

Medical apparatus system 22 obtains (800) device characteristics, as detailed above, from medical device 10 of a prospective patient. In various embodiments, system obtains the device characteristics by database 26 obtaining the device characteristics via network 24. Alternatively, analyzer 27 obtains the device characteristics wherever analyzer 27 is located in system 22. System 22 may optionally further obtain (802) patient characteristics, as detailed above, from the prospective patient.

System 22 accesses (804) historical database 26 which already incorporates device characteristics and an assessment of efficacy of therapy of a multiplicity of patients who have already received a medical device 10 and received a clinical therapy. Optionally, historical database 26 further incorporates patient characteristics from the multiplicity of patients. In various embodiments, historical database 26 is created (806) and updated frequently with data from new patients and, optionally, the prospective patient. In such embodiments, historical database 26 is constantly or continually updated with data from patients, in certain cases all patients, across a network of medical devices, routinely incorporating new information about symptoms, applied therapies and the success of those therapies as new information is developed on a patient-by-patient and device-by-device basis. In such embodiments, routinely incorporating new information may tend to expand the ability of historical database 26 to provide pertinent information for recommending new prospective therapy recommendations to new and existing patients. Alternatively, historical database 26 is obtained from an alternative source, such as from a third-party vendor.

Medical apparatus system 22 correlates (808) the device characteristics from medical device 10 of the prospective patient with the device characteristics and assessment of efficacy of clinical therapy of the multiplicity of patients. In various embodiments, analyzer 27 performs the correlation. In various embodiments, the correlation occurs using a Bayesian method, a self-organizing map or various alternative statistical analysis methods. When patient characteristics are obtained (802) patient characteristics may be included in the correlation along with patient characteristics from the multiplicity of patients.

A prospective clinical therapy is identified (810) utilizing historical database 26 and based, at least in part, on the correlation. In the exemplary embodiment detailed above, the prospective clinical therapy may be the product of multiple applications of the self-organizing map procedure for various combinations of symptoms and clinical therapies. In such embodiments, the prospective clinical therapy may be the one therapy with the most binary indications of effectivity 76. In other words, the prospective clinical therapy may be one clinical therapy deemed to have the greatest likelihood of success if applied to the prospective patient. Alternatively, more than one prospective therapy may be recommended if the likelihood of success for each is determined to be the same or adequately similar as other prospective therapies.

Upon identifying the prospective clinical therapy, the prospective clinical therapy may be presented (812) to a user, in an embodiment using terminal 28. In various embodiments, the prospective clinical therapy may be presented with additional information, including an anticipated likelihood of success and alternative prospective therapies which may be deemed to have a relatively high likelihood of success. In various embodiments, the process of FIG. 8 may be repeated periodically to provide new or adjusted prospective clinical therapies to treat the prospective patient in view of changing circumstances of the prospective patient and new information which may have been acquired by historical database 26.

Thus, embodiments of the system and method for identifying a prospective clinical therapy for a prospective patient having a medical device are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A system for identifying a prospective clinical therapy for a prospective patient having a medical device, performed with a medical apparatus, comprising:

A data storage device configured to store a historical database incorporating information relating to a multiplicity of patients, each of said multiplicity of patients having a medical device and each of said multiplicity of patients having undergone at least one of a plurality of clinical therapies, said information comprising, for each of said multiplicity of patients, device characteristics of said medical device, patient characteristics of each of said multiplicity of patients and an assessment of efficacy of the clinical therapies;

wherein said plurality of clinical therapies are delivered by the medical device associated with said multiplicity of patients; and an analyzer comprising electronic equipment configured to correlate device characteristics of said prospective patient with said device characteristics, said patient characteristics and said assessment of efficacy of clinical therapies of said multiplicity of patients using said historical database to identify a prospective clinical therapy for said prospective patient associated with said device characteristics in said historical database having a relatively greater efficacy than one of plurality of said clinical therapies;

wherein said prospective clinical therapy is delivered by the medical device associated with said prospective patient;

wherein said correlating step is accomplished utilizing statistical analysis.

2. The system as in claim 1 further comprising an output configured to provide said prospective clinical therapy to a user.

3. The system as in claim 1 wherein said device characteristics comprise at least one of atrial tachycardia burden, atrial fibrillation burden, atrial tachycardia episode duration, atrial fibrillation episode duration, ventricular rate during at least one of atrial tachycardia and atrial arrhythmia, patient activity, heart rate, heart rate variability, defibrillation shocks, ventricular tachycardia, ventricular fibrillation, attempts at ventricular antitachycardia pacing, success at ventricular antitachycardia pacing, attempts at atrial antitachycardia pacing, success at atrial antitachycardia pacing, thoracic impedance, respiration, pressure, heart sounds, electrocardiogram timing, electrocardiogram morphology, proportion of atrial pacing, proportion of ventricular pacing, bradycardia episodes, asystole episodes, premature atrial contractions, premature ventricular contractions, patient inputs indicative of symptomatic episodes and patient-initiated shocks.

4. The system as in claim 1 wherein said patient characteristics comprise at least one of age, gender, body mass index, weight, blood pressure, prior hospitalizations, family history of disease, symptom status, New York Heart Association classification, medications being taken, prior cardiovascular surgeries/procedures, left ventricular ejection fraction, left atrial diameter, cardiac output, left ventricular chamber dimensions, values indicative of quality of life, functional capacity measure, CHADS2 score, congestive heart failure, diabetes, hypertension, prior stroke or transient ischemic attack, coronary artery disease, atrial tachyarrhythmia, ventricular tachyarrhythmia, bradycardia, valvular disease and myocardial infarction.

5. The system as in claim 1 wherein said statistical analysis comprises Bayesian methods.

6. The system as in claim 1 wherein said statistical analysis comprises self-organizing maps.

7. A method of identifying a prospective clinical therapy for a prospective patient having a medical device, performed by medical apparatus, comprising the steps of:
   obtaining, by said medical apparatus, device characteristics from said medical device of said prospective patient;
   accessing, by said medical apparatus, a historical database incorporating information relating to a multiplicity of patients, each of said multiplicity of patients having received a medical device and each of said multiplicity of patients having undergone a at least one of a plurality of clinical therapies, said information comprising, for each of said multiplicity of patients, device characteristics of said medical device associated with said multiplicity of patients, patient characteristics of each of said multiplicity of patients and an assessment of an efficacy of said plurality of clinical therapies;
   wherein said plurality of clinical therapies are delivered by the medical device associated with said multiplicity of patients; and
   correlating, by said medical apparatus, said device characteristics of said prospective patient with said device characteristics of the medical device associated with said multiplicity of patients, said patient characteristics and said assessment of efficacy of at least one of said plurality of clinical therapies of said multiplicity of patients; and
   identifying, by said medical apparatus, using said historical database, a prospective clinical therapy for said prospective patient associated with said device characteristics and said patient characteristics in said historical database based on said correlation, wherein said prospective clinical therapy having a relatively greater efficacy than at least one of said plurality of clinical therapies;
   wherein said prospective clinical therapy is delivered by the medical device associated with said prospective patient;
   wherein said correlating step is accomplished utilizing statistical analysis.

8. The method as in claim 7 further comprising a step of creating said historical database incorporating information relating to a multiplicity of patients, each of said multiplicity of patients having received a medical device and each of said multiplicity of patients having undergone at least one of a plurality of clinical therapies, said information comprising, for each of said multiplicity of patients, device characteristics of said medical device, patient characteristics and an assessment of an efficacy of at least one of said plurality of clinical therapies.

9. The method as in claim 7 further comprising a step of recommending, with said medical apparatus, to a physician said prospective clinical therapy.

10. The method as in claim 7 wherein said device characteristics comprise at least one of atrial tachycardia burden, atrial fibrillation burden, atrial tachycardia episode duration, atrial fibrillation episode duration, ventricular rate during at least one of atrial tachycardia and atrial arrhythmia, patient activity, heart rate, heart rate variability, defibrillation shocks, ventricular tachycardia, ventricular fibrillation, attempts at ventricular antitachycardia pacing, success at ventricular antitachycardia pacing, attempts at atrial antitachycardia pacing, success at atrial antitachycardia pacing, thoracic impedance, respiration, pressure, heart sounds, electrocardiogram timing, electrocardiogram morphology, proportion of atrial pacing, proportion of ventricular pacing, bradycardia episodes, asystole episodes, premature atrial contractions, premature ventricular contractions, patient inputs indicative of symptomatic episodes and patient-initiated shocks.

11. The method as in claim 7 wherein said patient characteristics comprise at least one of age, gender, body mass index, weight, blood pressure, prior hospitalizations, family history of disease, symptom status, New York Heart Association classification, medications being taken, prior cardiovascular surgeries/procedures, left ventricular ejection fraction, left atrial diameter, cardiac output, left ventricular chamber dimensions, values indicative of quality of life, functional capacity measure, CHADS2 score, congestive heart failure, diabetes, hypertension, prior stroke or transient ischemic attack, coronary artery disease, atrial tachyarrhythmia, ventricular tachyarrhythmia, bradycardia, valvular disease and myocardial infarction.

12. The method as in claim 7 wherein said statistical analysis comprises Bayesian methods.

13. The method as in claim 7 wherein said statistical analysis comprises self-organizing maps.

* * * * *

UNITED STATES PATENT AND TRADEMARK OFFICE
CERTIFICATE OF CORRECTION

PATENT NO.       : 8,688,469 B2                                                  Page 1 of 1
APPLICATION NO.  : 12/915945
DATED            : April 1, 2014
INVENTOR(S)      : Paul D. Ziegler et al.

It is certified that error appears in the above-identified patent and that said Letters Patent is hereby corrected as shown below:

In The Claims

Col. 12, line 37, delete "than one of plurality of said clinical" and insert in place thereof -- than one of said plurality of clinical --;

Col. 13, line 15, delete "performed by medical apparatus, comprising" and insert in place thereof -- performed by a medical apparatus, comprising --;

Col. 13, line 22, delete "undergone a at least one of a plurality" and insert in place thereof -- undergone at least one of a plurality --.

Signed and Sealed this
Eighth Day of March, 2016

Michelle K. Lee
*Director of the United States Patent and Trademark Office*